United States Patent [19]
Waldock et al.

[11] Patent Number: 5,484,447
[45] Date of Patent: Jan. 16, 1996

[54] CALIPERS FOR USE IN OPHTHALMIC SURGERY

[75] Inventors: Terence A. Waldock, Meppershall; John L. Pearce, Bromsgrove, both of England

[73] Assignee: Duckworth & Kent Limited, England

[21] Appl. No.: 280,427

[22] Filed: Jul. 26, 1994

[51] Int. Cl.⁶ .................................................. A61B 17/00
[52] U.S. Cl. ........................... 606/107; 606/107; 606/198; 606/205; 33/511
[58] Field of Search ................... 606/107, 161, 606/167, 172, 174, 191, 198, 205; 33/511, 512, 783, 807, 808

[56] References Cited

U.S. PATENT DOCUMENTS

| | | | |
|---|---|---|---|
| 1,221,668 | 4/1917 | Brunton | 33/808 |
| 1,226,337 | 5/1917 | Lackner | 33/808 |
| 1,303,797 | 5/1919 | Walton | 33/808 |
| 1,528,273 | 3/1925 | Shwed | 33/512 X |
| 3,740,779 | 6/1973 | Rubricuis | 606/167 X |
| 4,127,112 | 11/1978 | Sherlock et al. | 606/205 X |
| 4,390,059 | 7/1982 | Marinoff | 606/172 X |
| 5,235,748 | 8/1993 | Jahn | 33/783 X |

*Primary Examiner*—Sam Rimell
*Attorney, Agent, or Firm*—Seidel Gonda Lavorgna & Monaco

[57] ABSTRACT

A caliper for ophthalmic surgery comprises a pair of arms which are relatively pivotable, with each arm terminating at one end in a tip, and with the tips being movable between closed and open positions upon pivotal movement of the arms. The amount of pivoting movement is controlled by an adjuster and a scale is provided to give an indication of the amount of tip separation. The tips of the arms are adapted to be insertable into an incision in eye tissue and to open the incision to a predetermined dimension to permit the insertion of an ocular lens. The tips may open the incision just by a stretching of the eye tissue, for subsequent insertion of the lens, or alternatively the tips may be provided with one or two diamond blades which open the incision by a cutting of the eye tissue.

7 Claims, 4 Drawing Sheets

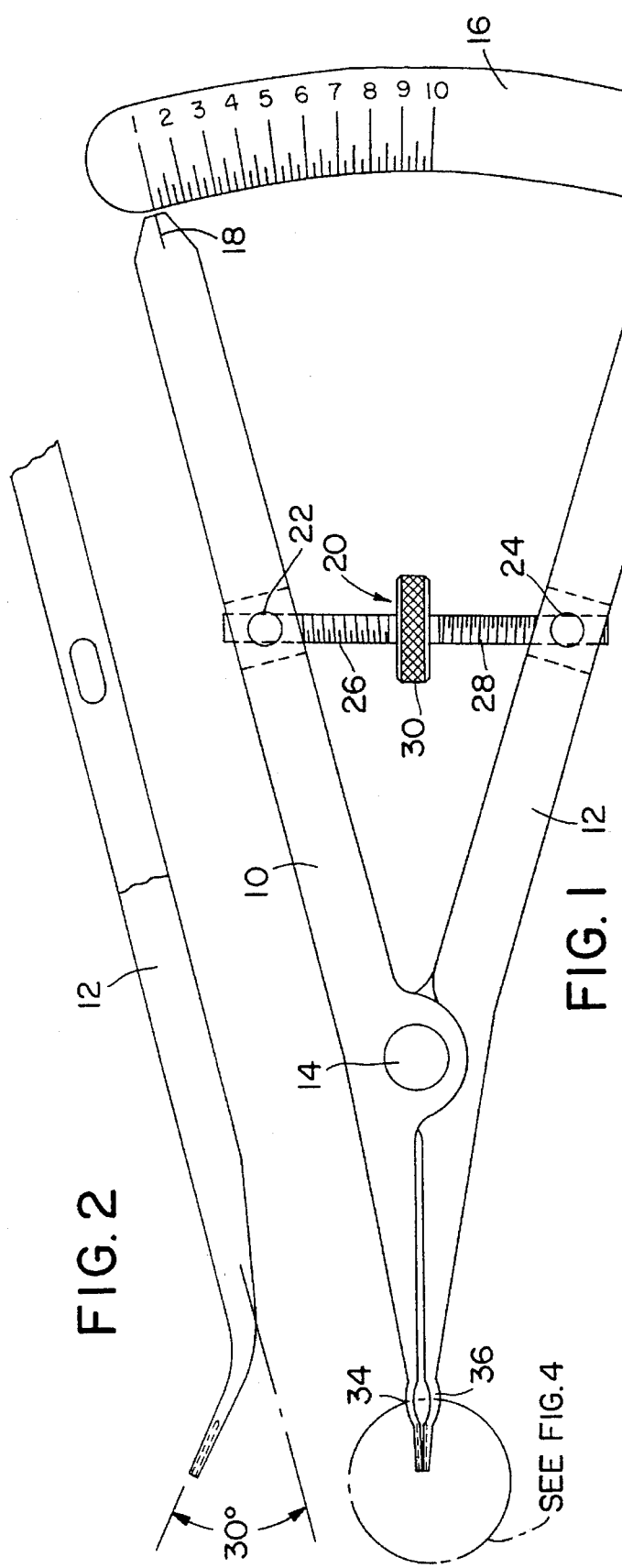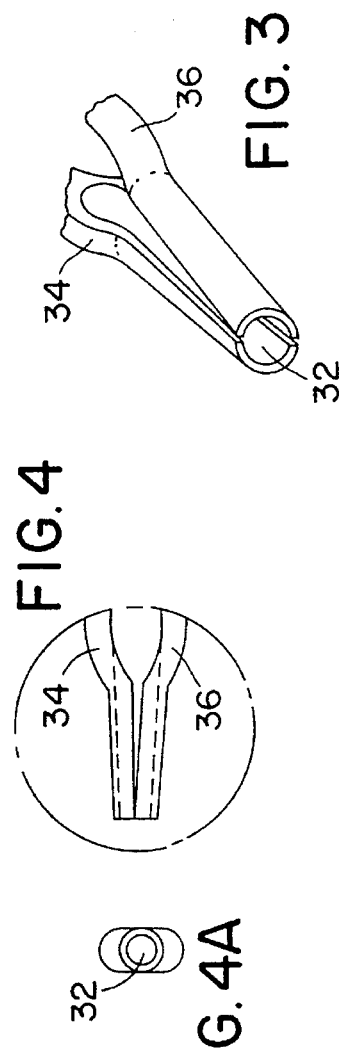

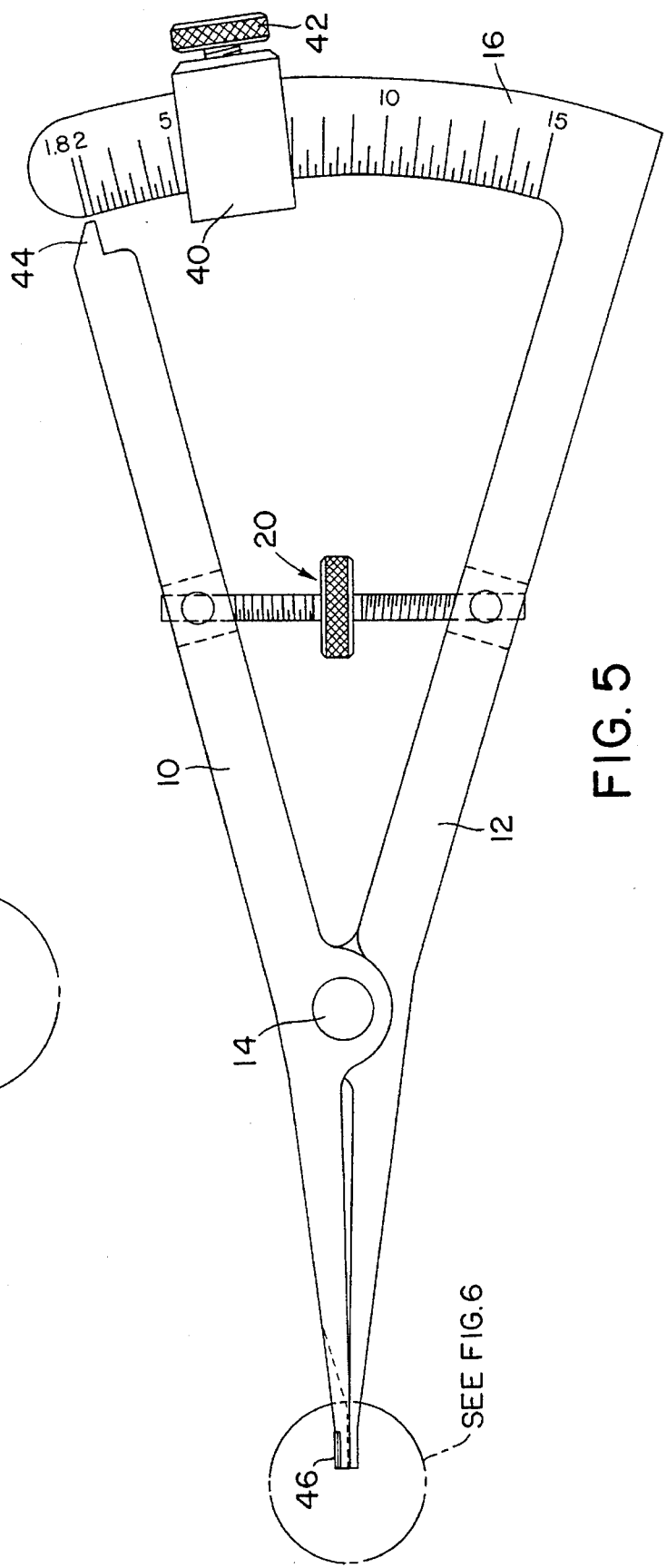

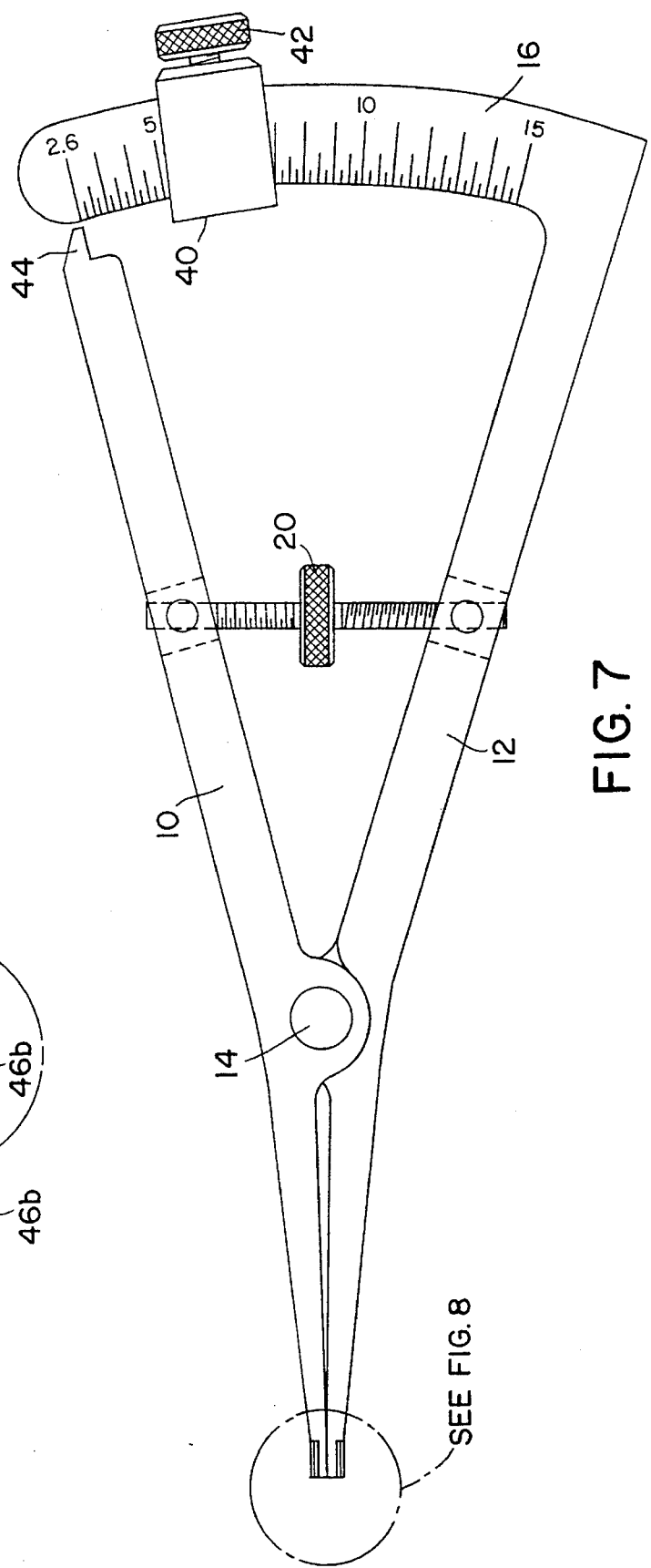

5,484,447

CALIPERS FOR USE IN OPHTHALMIC SURGERY

FIELD OF THE INVENTION

This invention relates to calipers for use in ophthalmic surgery.

BACKGROUND OF THE INVENTION

Calipers for use in ophthalmic surgery are known. Conventionally, such calipers are used to measure an incision in the eye, especially to measure the width of an incision prior to the insertion of a lens. Other calipers are used as marking instruments to make marks on the eye tissue to aid the surgeon in making an incision.

SUMMARY OF THE INVENTION

It is an object of the present invention to provide an improved caliper for ophthalmic surgery which can be used as an aid in the making of an incision to the desired dimension for the insertion of an ocular lens. The calipers of the present invention are adapted to be used in particular for ophthalmic surgery where the lens of the eye is to be replaced by an artificial lens.

It is a further object of the present invention to provide a caliper for ophthalmic surgery which enables an incision in the eye tissue to be made to an extremely accurate dimension in a simple and reliable way.

In accordance with the invention there is provided a caliper for ophthalmic surgery comprising a pair of arms which are relatively pivotable about a pivot axis, each arm terminating at one end in a tip with the tips movable between closed and open positions upon said pivoting movement, adjusting means to permit controlled pivoting movement of said arms, and scale means to provide an indication of the amount of tip separation, wherein the tips of the arms are adapted to be insertable into an incision in eye tissue and to open the incision to a predetermined dimension to permit the insertion of an ocular lens.

In one embodiment of the invention the tips open the incision by a stretching of the eye tissue.

In an alternative embodiment of the invention, the tips open the incision by a cutting of the eye tissue, for example by the use of a cutting blade, e.g. a diamond blade, on one or both of the tips of the arms.

Preferably, one arm is a pointer arm having a pointer at its end remote from the tip, and the other arm is a scale arm carrying a scale at its end remote from the tip, with the pointer moving over the scale as pivoting of the arms takes place. The scale arm may carry an adjustable setting stop for cooperative abutment by the pointer when the predetermined dimension is achieved.

The calipers of the present invention are preferably made of titanium, with the use of diamond blades if the tips are provided with a cutting function.

BRIEF DESCRIPTION OF THE DRAWINGS

In order that the invention may be fully understood, a description will now be given of a number of embodiments of caliper in accordance with the invention. These are given by way of example and with reference to the accompanying drawings. In the drawings:

FIG. 1 is a plan view of a first embodiment of caliper adapted to assist in the insertion of a lens;

FIG. 2 is a side view of the forward end of the caliper of FIG. 1;

FIG. 3 is an oblique view of the tip of the caliper of FIG. 1;

FIG. 4 is a view on an enlarged scale of the tips of the caliper arms;

FIG. 4A is an end view on an enlarged scale of the tips of the caliper arms;

FIG. 5 is a plan view of a second embodiment of caliper in accordance with the invention, having a single cutting blade;

FIG. 6 is a view on an enlarged scale of the tip portion of the caliper arms in FIG. 5;

FIG. 6A is an end view on an enlarged scale of the tip portion of the caliper arms in FIG. 5;

FIG. 7 is a plan view of a third embodiment of caliper in accordance with the invention, having two cutting blades;

FIG. 8 is a view on an enlarged scale of the tip portion of the caliper of FIG. 7; and, FIG. 8A is an end view on an enlarged scale of the tip portion of the caliper of FIG. 7.

DESCRIPTION OF THE PREFERRED EMBODIMENTS

Figure 9:
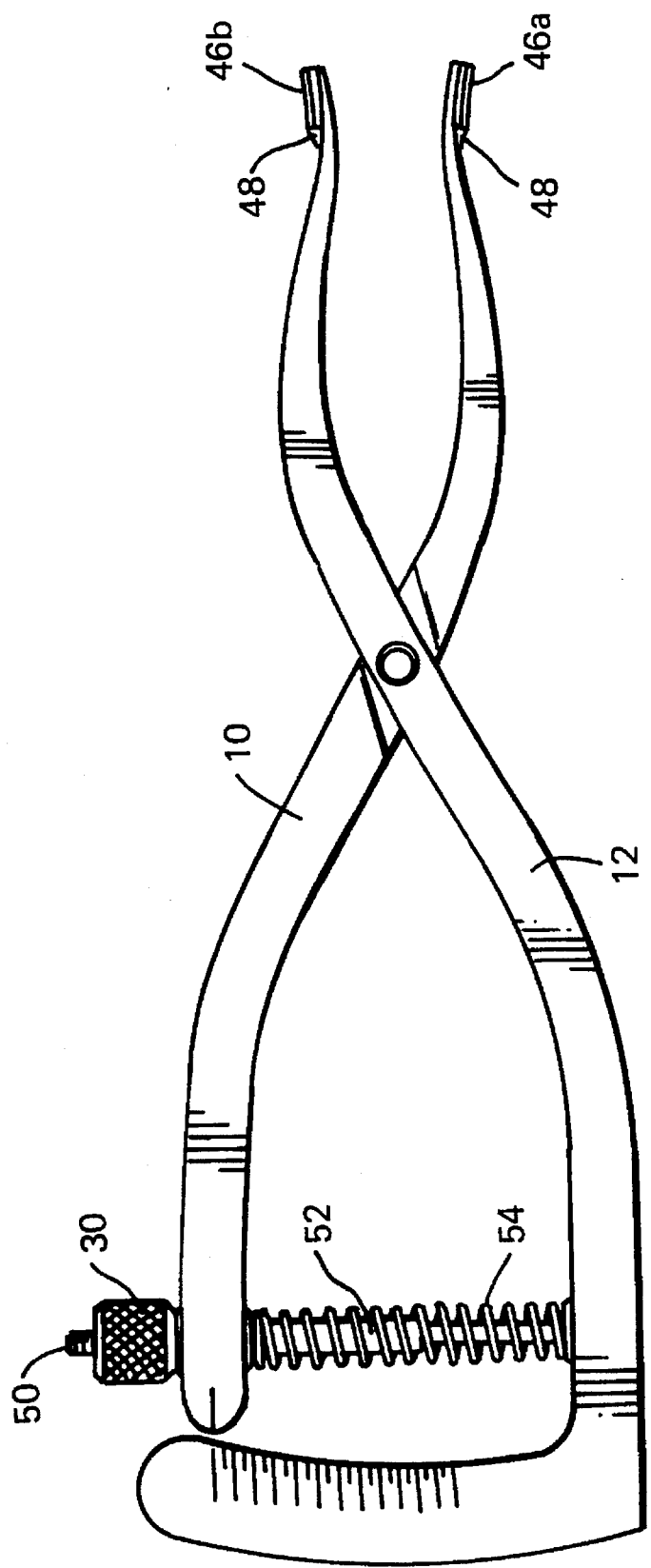
FIG. 9 is a plan view of a fourth embodiment of caliper in accordance with the invention having two cutting blades and with a modified adjuster mechanism.

In the various embodiments, the same or equivalent components are given the same reference numerals.

Referring first to FIGS. 1 to 4, there is shown an embodiment of caliper in accordance with the invention which is a lens insertion caliper and which is designed to enable the surgeon to open an incision by a stretching of the eye tissue, thereby to assist in the insertion of a lens. The caliper comprises a pointer arm 10 and a scale arm 12 which are connected for relative pivotal movement about a pivot pin 14. The scale arm 12 is provided with an arcuate extension 16 which bears scale markings which are indicative of the separation of the arms at the tip end. The rearward end of the pointer arm 10 moves in an arc and cooperates with the scale markings on the scale arm extension 16. The rearward end of the pointer arm 10 is provided with a centre mark 18 to enable the exact dimension at the tip end to be read off.

The pivotal movement of the two arms 10 and 12 is controlled by an adjuster mechanism indicated generally at 20. The pointer arm 10 is fitted with a left-hand threaded nut 22 and the scale arm 12 is fitted with a right-hand threaded nut 24. A first screw-threaded rod 26 is associated with the left-hand threaded nut 22 and a second screw-threaded rod 28 is associated with the right-hand threaded nut 24. A knurled knob 30 is set between the adjacent ends of the two rods 26 and 28. Thus, rotation of the knurled knob 30 will cause the two arms 10, 12 either to be drawn together or pushed apart, with consequent movement at the tips of the arms.

The tip ends of the two arms 10 and 12 are turned up as shown most clearly in FIG. 2, at an angle of about 30° to the general longitudinal axis of the arms. This is to assist in the insertion of a lens using the caliper. The tips of the arms converge to meet at the forward end when the caliper is closed. Each tip is of substantially semi-circular cross-section, thereby to define a central channel 32. To the rear of the actual tips, the arms are each provided with an arcuate outward protuberance 34, 36. The channels which run through the tips of the arms terminate in this protuberant zone. The protuberant portions of the arms define an internal pocket within which a lens can be positioned with the tips closed. In use, after an initial incision has been made in the eye tissue, for example in the cornea, the tips of the caliper are inserted into the incision and by operation of the knurled knob 30 the tips are opened to the predetermined dimension, whereupon the lens is able to slide from the pocket in the arms down through the channel 32 and into place within the eye. The length of the tip portion of each arm, from the forward end to the protuberant zone 34, 36, is of the order of 4 mm.

So far as materials are concerned, the caliper arms 10 and 12 are preferably made of titanium. The adjusting rods 26 and 28 and the knob 30 are preferably coated with titanium nitride.

A second embodiment of caliper in accordance with the invention is shown in FIGS. 5 and 6. The general structure of the caliper is similar to that of the first embodiment described above. However, in this embodiment the scale arm extension 16 is fitted with a setting stop 40 which can be tightened and loosened on the scale arm extension by operation of a knurled knob 42. The rearward end of the pointer arm 10 is cut back to a centre line to define a finger 44 which is intended to abut against the setting stop 40. In this embodiment the tip of one of the arms, here the pointer arm 10, is provided with a cutting blade, preferably a diamond blade. This is shown most clearly in the enlarged views of FIGS. 6 and 6A which shows the tips of the arms both in side elevation and end elevation. The cutting blade 46 is mounted at the arm tip by a glue fillet. An epoxy resin may be used such as that known by the trade mark "Araldite". The length of the cutting blade is approximately 3 mm. It will be seen also that the depth of the tip of the scale arm 12 is less than that of the pointer arm 10 which carries the blade. The outward face of the tip of the scale arm 12 is flat.

In use, the surgeon will make a small incision in the eye tissue. Having set the stop 40 to the desired dimension the tips of the caliper are inserted into the incision and by use of the adjuster mechanism 20 the tips are moved apart, thereby widening the incision until the pointer arm finger 44 strikes the stop and the incision has been enlarged to the correct dimension.

FIGS. 7 and 8 show a third embodiment of caliper in accordance with the invention. This embodiment is very similar to that shown in FIG. 5 and 6, except that a cutting blade is mounted at the tip of each arm 10, 12. These blades are indicated at 46a and 46b. Again, the blades are glued in place at the tips of the arms. As will be seen, in this embodiment the tips of the arms are of the same dimension, as compared with the previous embodiment where the scale arm tip was substantially slimmer than the other tip. This caliper is used in substantially the same way as the single blade caliper, with the provision of the two blades being preferred for certain surgical procedures. Once the incision has been enlarged by cutting to the desired dimension then a lens can be inserted into the eye.

FIG. 9 shows a fourth embodiment of caliper in accordance with the invention. This again is a double blade caliper, with diamond blades 46a and 46b. It will be noted from FIG. 9 that the zone immediately behind each of the blades 46a, 46b is filled with glue, as indicated at 48, in order not to leave a "step" between the blade and the caliper arm. The difference between this caliper and the double-blade caliper of FIGS. 7 and 8 is in the form of the adjuster mechanism. Here the adjusting knob 30 is positioned outside the caliper arms instead of mid-way between them. The adjusting nut 30 is mounted on an adjusting rod 50 which extends through the pointer arm 10 and is pivotally mounted in the scale arm 12. In the zone between the caliper arms the adjusting rod is enclosed by a spring sleeve 52 and by a helical spring 54. By rotation of the adjusting knob 30 the pointer arm 10 is moved against the spring bias to any desired setting as indicated by the rearward end of the pointer arm.

We claim:

1. A caliper for ophthalmic surgery comprising a pair of arms which are relatively pivotable about a pivot axis, each arm terminating at one end in a tip with the tips movable between closed and open positions upon said pivot movement, an outwardly directed cutting blade carried by one of the tips, adjusting means to permit controlled pivoting movement of said arms, and scale means to provide an indication of the amount of tip separation, wherein the tips of the arms are adapted to be insertable into an incision in eye tissue and to open the incision to a predetermined dimension by cutting to permit the insertion of an ocular lens.

2. A caliper according to claim 1, in which the cutting blade is a diamond blade.

3. A caliper for ophthalmic surgery comprising a pair of arms which are relatively pivotable about a pivot axis, each arm terminating at one end in a tip with the tips movable between closed and open positions upon said pivot movement, an outwardly directed cutting blade carried by each tip, adjusting means to permit controlled pivoting movement of said arms, and scale means to provide an indication of the amount of tip separation, wherein the tips of the arms are adapted to be insertable into an incision in eye tissue and to open the incision to a predetermined dimension by cutting to permit the insertion of an ocular lens.

4. A caliper according to claim 3, in which the cutting blades are diamond blades.

5. A caliper for ophthalmic surgery comprising a pair of arms which are relatively pivotable about a pivot axis, each arm terminating at one end in a tip with the tips movable between closed and open positions upon said pivot movement, in which the arms are arcuately shaped at a position rearwardly of the tips to define an internal pocket for an ocular lens and the arms have respective confronting channels therein from the pocket to the forward end of the tips through which the lens can slide upon insertion into the eye, adjusting means to permit controlled pivoting movement of said arms, and scale means to provide an indication of the amount of tip separation, wherein the tips of the arms are adapted to be insertable into an incision in eye tissue and to open the incision to a predetermined dimension by cutting to permit the insertion of an ocular lens.

6. A caliper according to claim 5, in which the tips extend at an angle of the order of 30° to the axes of the parts of the arms to the rear of the tips.

7. A caliper for ophthalmic surgery comprising a pair of arms which are relatively pivotable about a pivot axis, each arm terminating at one end in a tip with the tips movable between closed and open positions upon said pivot movement, in which one arm is a pointer arm having a pointer at its end remote from the tip, and the other arm is a scale arm carrying a scale at its end remote from the tip, the pointer moving over the scale as pivoting of the arms takes place wherein the scale arm carries an adjustable setting stop for cooperative abutment by the pointer when a preselected position is reached, an outwardly directed cutting blade carried by one of the tips, adjusting means to permit controlled pivoting movement of said arms, wherein the tips of the arms are adapted to be insertable into an incision in eye tissue and to open the incision to a predetermined dimension by cutting to permit the insertion of an ocular lens.

* * * * *

UNITED STATES PATENT AND TRADEMARK OFFICE
CERTIFICATE OF CORRECTION

PATENT NO. : 5,484,447

DATED : January 16, 1996

INVENTOR(S) : Terence A. Waldock, et al.

It is certified that error appears in the above-indentified patent and that said Letters Patent is hereby corrected as shown below:

Claim 5, Column 4, line 56 change "cutting" to -- stretching --.

Signed and Sealed this

Twentieth Day of May, 1997

Attest:

BRUCE LEHMAN

Attesting Officer

Commissioner of Patents and Trademarks